United States Patent
Ono (10) Patent No.: US 9,232,196 B2
(45) Date of Patent: Jan. 5, 2016

(54) IMAGE CAPTURING APPARATUS AND ENDOSCOPE SYSTEM

(75) Inventor: Shuji Ono, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 997 days.

(21) Appl. No.: 13/216,384

(22) Filed: Aug. 24, 2011

(65) Prior Publication Data

US 2012/0050512 A1   Mar. 1, 2012

(30) Foreign Application Priority Data

Aug. 24, 2010   (JP) ................. 2010-187630

(51) Int. Cl.
| | |
|---|---|
| *A62B 1/04* | (2006.01) |
| *H04N 7/18* | (2006.01) |
| *A61B 1/00* | (2006.01) |
| *A61B 1/05* | (2006.01) |
| *H04N 5/225* | (2006.01) |

(52) U.S. Cl.
CPC ............ *H04N 7/183* (2013.01); *A61B 1/00009* (2013.01); *A61B 1/00181* (2013.01); *A61B 1/05* (2013.01); *H04N 2005/2255* (2013.01)

(58) Field of Classification Search
CPC .......................................... H04N 2005/2255
See application file for complete search history.

(56) References Cited

U.S. PATENT DOCUMENTS

| | | | | |
|---|---|---|---|---|
| 6,063,023 A | * | 5/2000 | Sakiyama et al. | 600/118 |
| 2006/0183992 A1 | * | 8/2006 | Kawashima | 600/407 |

FOREIGN PATENT DOCUMENTS

| | | |
|---|---|---|
| JP | 2006-322796 A | 11/2006 |
| JP | 2009-103980 A | 5/2009 |

* cited by examiner

*Primary Examiner* — Chikaodili E Anyikire
(74) *Attorney, Agent, or Firm* — Sughrue Mion, PLLC (57) ABSTRACT

An image-capturing apparatus includes: an image-capturing section including a first image-capturing system and a second image-capturing system having an image-capturing optical axis on a different position from that of the first image-capturing system and a different image-capturing characteristic from the first image-capturing system; a positional-relation specifying section specifying a first positional-relation between the first image-capturing system and a subject at a first timing at which the first image-capturing system has performed image-capturing; a judging section judging whether a second positional-relation between the second image-capturing system and the subject matches more the first positional-relation at a second timing, based on a displacement of the image-capturing apparatus with respect to the subject by the first image-capturing system, positions of image-capturing optical axes respectively of the first image-capturing system and the second image-capturing system, and the first positional-relation; and an image combining section combining the first image with the second image.

19 Claims, 6 Drawing Sheets

IMAGE CAPTURING APPARATUS AND ENDOSCOPE SYSTEM

The contents of the following Japanese patent application are incorporated herein by reference, No. 2010-187630 filed on Aug. 24, 2010.

BACKGROUND

1. Technical Field

The present invention relates to an image capturing apparatus and an endoscope system.

2. Related Art

A technology of serially capturing two images while panning at the position closest to the parallax of both eyes, and setting them as the left eye image and the right eye image is already known (refer to Patent Document No. 1 for example). Moreover, a technology of predicting the arrival point of the car and limiting the operation-target range of computing the object distance from an image obtained in the car is already known (refer to Patent Document No. 2 for example). The following shows the specifics of the patent documents cited above.

Patent Document No. 1: Japanese Patent Application Publication No. 2009-103980
Patent Document No. 2: Japanese Patent Application Publication No. 2006-322796

SUMMARY

The images obtained by a plurality of cameras contain a parallax difference due to the difference in perspectives. Such a large parallax difference can be inconvenient, except in such cases as spectroscopic image capturing or distance measuring where the parallax difference is effectively used.

Therefore, according to a first aspect of the innovations herein, provided is an image capturing apparatus including: an image capturing section that includes a first image capturing system and a second image capturing system, the second image capturing system having an image capturing optical axis on a different position from an image capturing optical axis of the first image capturing system and a different image capturing characteristic from an image capturing characteristic of the first image capturing system; a positional relation specifying section that specifies a first positional relation between the first image capturing system and a subject at a first timing at which the first image capturing system has captured an image of the subject; a judging section that judges whether a second positional relation between the second image capturing system and the subject matches more the first positional relation at a second timing than the first timing, based on a displacement of the image capturing apparatus with respect to the subject captured by the first image capturing system, positions of image capturing optical axes respectively of the first image capturing system and the second image capturing system, and the first positional relation; and an image combining section that combines a first image of the subject captured by the first image capturing system at the first timing, with a second image of the subject captured by the second image capturing system at the second timing.

The image capturing apparatus may further include: a movement information obtaining section that obtains movement information indicating an amount of movement of the image capturing apparatus, where the judging section judges whether the second positional relation matches more the first positional relation at the second timing than the first timing, based on the amount of movement indicated by the movement information, the positions of the image capturing optical axes respectively of the first image capturing system and the second image capturing system, and a positional relation specified by the positional relation specifying section.

The positional relation specifying section may specify, as the first positional relation, a relative position of the first image capturing system with respect to the subject and an orientation of the image capturing optical axis of the first image capturing system at the first timing, and the judging section may judge whether the relative position of the second image capturing system with respect to the subject and the orientation of the image capturing optical axis of the second image capturing system match more the first positional relation at the second timing than the first timing.

The image capturing apparatus may further include: an image capturing control section that controls the second image capturing system to perform image capturing at the second timing, when the judging section has judged that the second positional relation matches more the first positional relation at the second timing than the first timing after the first image capturing system has performed image capturing at the first timing.

The image capturing apparatus may further include: an image storage section that stores a plurality of images captured by the second image capturing system at different timings, where for each image stored in the image storage section, the judging section judges whether the second positional relation in a timing at which the image has been captured matches the first positional relation more than the first timing, and the image combining section selects, from among the images whose second positional relation is judged to match more the first positional relation, an image whose matching degree of the second positional relation with respect to the first positional relation is greater than a pre-set value, and combines the selected image with the first image.

The first image capturing system and the second image capturing system may capture serially capture images at substantially the same image capturing timings as each other, and the image storage section may store the plurality of images respectively captured by the first image capturing system and the second image capturing system, in association with information indicating respective image capturing timings.

The image capturing section may further include a third image capturing system whose image capturing optical axis and image capturing characteristic are different from image capturing optical axes and image capturing characteristics respectively of the first image capturing system and the second image capturing system, where the judging section further judge whether a third positional relation between the third image capturing system and the subject matches more the first positional relation at a third timing than the first timing, based on the displacement, the positions of image capturing optical axes respectively of the first image capturing system and the third image capturing system, and the first positional relation, and the image combining section combine the first image and the second image with a third image of the subject captured by the third image capturing system at the third timing.

A plurality of image capturing systems included in the image capturing section may capture an image of the subject by means of rays of light in wavelength regions different from each other.

In the image capturing section, an optical system included in each image capturing system may be different at least in one of focal length, focus distance, field depth, and F value, from the optical systems included in the other image capturing systems.

A plurality of image capturing systems included in the image capturing section may respectively include a plurality of image capturing elements receiving light from the subject, and the plurality of image capturing elements respectively included in the plurality of image capturing systems included in the image capturing section may be formed on the same substrate.

The summary clause does not necessarily describe all necessary features of the embodiments of the present invention. The present invention may also be a sub-combination of the features described above. The above and other features and advantages of the present invention will become more apparent from the following description of the embodiments taken in conjunction with the accompanying drawings.

DESCRIPTION OF EXEMPLARY EMBODIMENTS

Hereinafter, (some) embodiment(s) of the present invention will be described. The embodiment(s) do(es) not limit the invention according to the claims, and all the combinations of the features described in the embodiment(s) are not necessarily essential to means provided by aspects of the invention.

Figure 1:
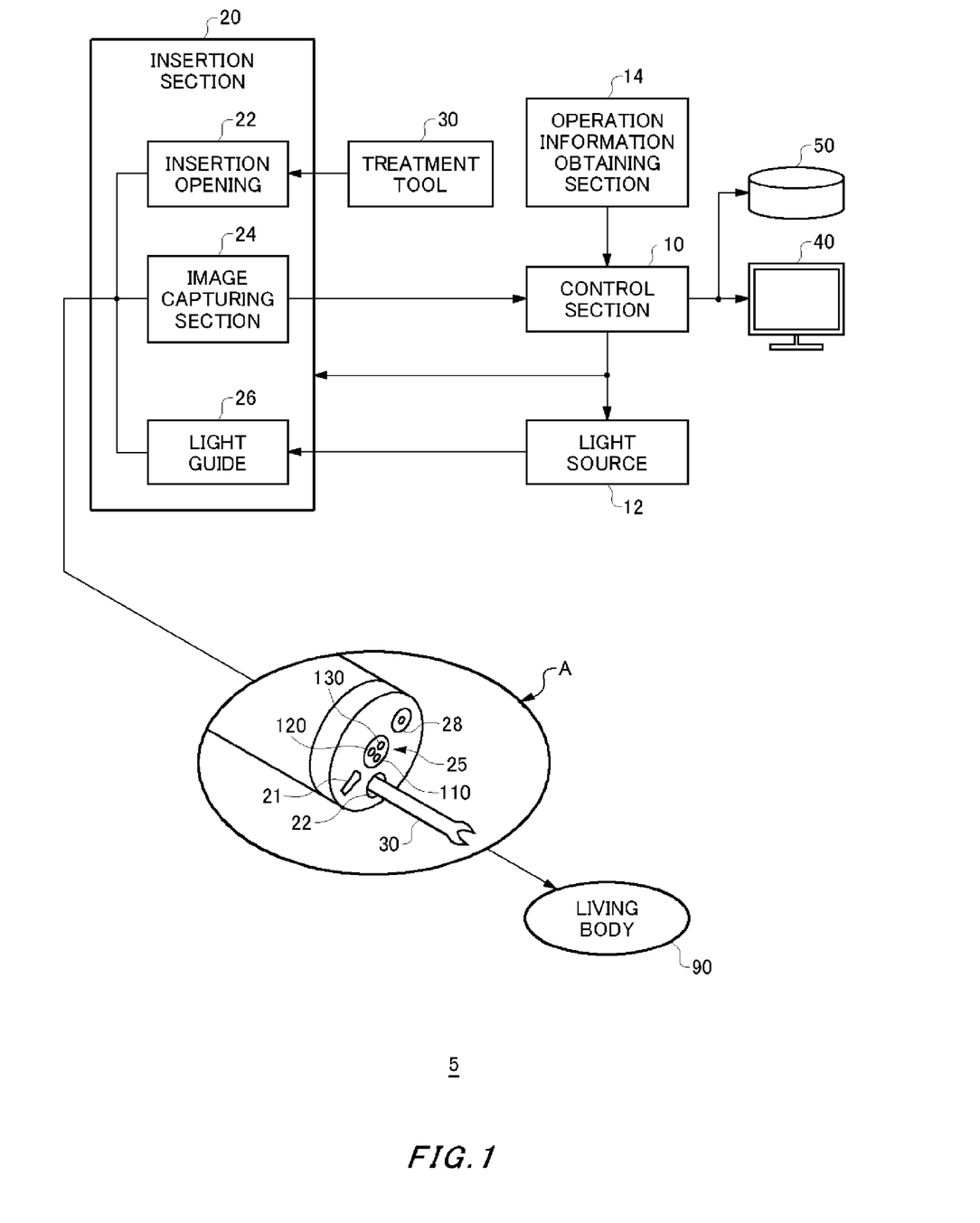
FIG. 1 shows an exemplary endoscope system 5 together with a living body 90 as a subject.

FIG. 1 shows an exemplary endoscope system 5 according to an embodiment, together with a living body 90 as an example of a subject. The endoscope system 5 provides an image having a comparatively small parallax difference. In an embodiment, the endoscope system 5 captures an image of a living body 90 through a plurality of objective lenses, while monitoring the positional relation between the plurality of objective lenses and the living body 90. During this process, the image capturing timing is controlled for each of the plurality of objective lenses, so as to capture an image of the living body 90 when a pre-set position relation between the objective lens and the living body 90 has been achieved. Accordingly, an image having a comparatively small parallax difference is provided.

The endoscope system 5 includes an insertion section 20, a light source 12, a control section 10, an operation information obtaining section 14, a recording apparatus 50, a display apparatus 40, and a treatment tool 30. Section A of the present drawing is an enlarged view of the tip of the insertion section 20. The living body 90 may an internal organ including the stomach, the intestine, or the like inside a living creature such as a person, for example.

The insertion section 20 includes an insertion opening 22, an image capturing section 24, and a light guide 26. The tip of the insertion section 20 includes an objective lens section 25 as part of the image capturing section 24. The objective lens section 25 includes a first lens 110, a second lens 120, and a third lens 130. The tip also includes a light irradiation opening 28 as part of the light guide 26. Each light irradiation opening 28 may be provided with an objective lens for light irradiation. The tip also includes a nozzle 21.

The insertion section 20 is a so-called endoscope and is inserted inside a living creature. The insertion section 20 is bendable, and by bending the insertion section 20, the orientation of the end surface of the insertion section 20 is controlled. The treatment tool 30 exemplified by forceps for treating the living body 90 is inserted in the insertion opening 22. The insertion opening 22 guides the inserted treatment tool 30 to the tip. The nozzle 21 transmits water or air toward the living body 90. The light guide 26 is mounted by an optical fiber, for example, and guides light such as irradiation light from the light source 12 towards the light irradiation opening 28. The light irradiation opening 28 irradiates the living body 90 with the light guided by the light guide 26. The image capturing section 24 captures images of the living body 90 by means of the light returned from the living body 90 respectively through the first lens 110, the second lens 120, and the third lens 130.

When the image capturing section 24 captures the image of the living body 90 using visible light, the light source 12 emits illumination light having a substantially white color. The irradiation light includes light of an R wavelength region, a G wavelength region, and a B wavelength region. The irradiation light is reflected by the living body 90 and scattered, and resulting light in a visible wavelength region is incident on the objective lens section 25 as returned light. The image capturing section 24 captures a visible light image by means of the light in the visible wavelength region returned from the living body 90. When the image capturing section 24 captures an image of the living body 90 using luminescence light such as fluorescent light, the light source 12 emits excitation light that excites a luminescence substance included in the living body 90. The luminescence light generated by exciting the luminescence substance by means of the excitation light is incident to the objective lens section 25, as the returned light.

The luminescence substance may be a substance injected into the living body 90 from outside, an example of which is indo cyanine green (ICG) emitting fluorescent light whose primary spectrum is in the 830 nm wavelength region. The luminescence substance may also be inherently contained in the components (e.g., cell) of the living body 90. An example of the inherent luminescence substance is a reduced NADH (nicotinamide adenine dinucleotide) emitting fluorescent light whose primary spectrum is in the 450 nm wavelength region. Another example of the inherent luminescence substance is FAD (flavin adenine dinucleotide) or collagen contained in connective tissue or the like of the living body.

The image capturing section 24 may capture an image of light of different wavelength regions in the visible light wavelength region used in image capturing and the luminescent light wavelength region, via different lenses of the plurality of lenses of the objective lens section 25. The image of the returned light in a specific wavelength region may be captured using a plurality of lenses. In addition, the image capturing may be conducted by time division for each wavelength region. In this case, the wavelength region of the returned light can be controlled in time division by controlling the wavelength region of the irradiation light from the light irradiation opening 28 in time division.

The control section 10 processes the image obtained by the image capturing section 24, and outputs the processed image to outside. For example, the control section 10 outputs the processed image to at least one of the recording apparatus 50 and the display apparatus 40. Specifically, the control section 10 combines the images respectively captured through the first lens 110, the second lens 120, and the third lens 130, to generate the processed image.

The operation information obtaining section 14 obtains a displacement instruction instructing to displace the insertion section 20, through an angle operation by a user or the like. The operation information obtaining section 14 is an example of an movement information obtaining section obtaining movement information representing the amount of movement of the insertion section 20. The operation information obtaining section 14 generates displacement instruction information based on the displacement instruction, and supplies the displacement instruction information to the control section 10. The control section 10 displaces the insertion section 20 based on the displacement instruction information.

To be specific, the control section 10 calculates the amount of displacement of the insertion section 20 based on the displacement instruction information, and displaces the insertion section 20 based on the calculated amount of displacement. The amount of displacement may be the amount of insertion of the insertion section 20 and the amount of bending of the insertion section 20. The amount of insertion may be the length of the insertion section 20 to be inserted and the speed of insertion representing the length to be inserted per hour. The amount of bending may be an angle at which the insertion section 20 should be bent and a bending angular speed representing the angle at which the insertion section 20 should be bent per hour.

In this way, by controlling the amount of insertion and the amount of bending, the control section 10 can control the position of the insertion section 20 and the orientation of the end surface of the insertion section 20. Based on these amounts of displacement, the control section 10 specifies the positional relation between each lens of the objective lens section 25 and the living body 90. For each lens, the control section 10 controls the timing at which the image capturing section 24 performs image capturing, so that the image capturing section 24 can capture an image at a timing in which a pre-set positional relation has been achieved with respect to the living body 90. Accordingly, the image capturing can be realized through each lens at timing at which a small perspective difference results. As a result, the image having a small parallax difference can be captured.

Figure 2:
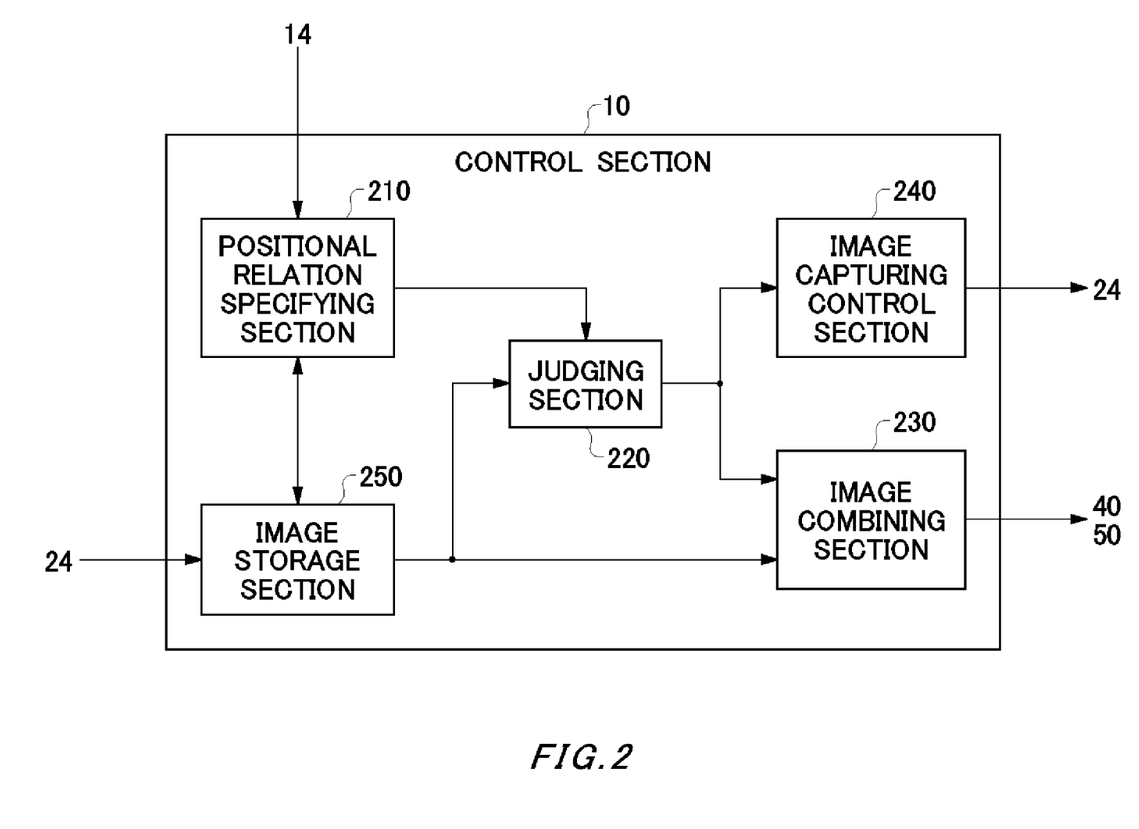
FIG. 2 schematically shows an exemplary block configuration of a control section 10.

FIG. 2 shows an exemplary block configuration of the control section 10. So as to prevent complex explanation, the functional block particularly related to image capturing control is shown from among the functional blocks of the control section 10. The control section 10 includes a positional relation specifying section 210, a judging section 220, an image combining section 230, an image capturing control section 240, and an image storage section 250.

The positional relation specifying section 210 obtains displacement information from the operation information obtaining section 14. The positional relation specifying section 210 specifies the positional relation, with respect to the living body 90, of each of the first lens 110, the second lens 120, and the third lens 130 at the timing of image capturing by the image capturing section 24, based on the displacement information supplied from the operation information obtaining section 14. The positional information specifying section 210 outputs, to the judging section 220, the information representing the displacement information and the positional information. In addition, the positional relation specifying section 210 outputs, to the image storage section 250, the information showing the positional relation.

The judging section 220 specifies the timing at which the image capturing section 24 should capture an image, based on the displacement of the insertion section 20, the positions of the optical axes of the first lens 110, the second lens 120, and the third lens 130, as well as the positional relation specified by the positional relation specifying section 210. Specifically, the judging section 220 judges whether each of the first lens 110, the second lens 120, and the third lens 130 has achieved a pre-set positional relation with respect to the living body 90. The judging section 220 may specify the displacement of the insertion section 20, based on the displacement information obtained from the operation information obtaining section 14.

The judging section 220 outputs the image capturing instruction to the image capturing control section 240, at the timing at which a pre-set positional relation has been achieved. The image capturing control section 240 controls the image capturing section 24 to capture an image of the living body 90, based on the image capturing instruction issued from the judging section 220.

The image storage section 250 obtains an image captured by the image capturing section 24 from the image capturing section 24, and temporarily stores it. The image storage section 250 supplies, to the judging section 220, the image obtained from the image capturing section 24. In addition, the image storage section 250 outputs, to the image combining section 230, the image obtained from the image capturing section 24 and the stored image. The image combining section 230 combines the images outputted from the image storage section 250, and outputs the combined image to at least one of the display apparatus 40 and the storage apparatus 50. Specifically, the image combining section 230 combines the images whose positional relation substantially matches, from among the images captured through the first lens 110, the second lens 120, and the third lens 130. Accordingly, the combined image of the images having comparatively a small parallax difference therebetween can be generated.

Note that the image storage section 250 may temporarily store the image obtained from the image capturing section 24, in association with the positional relation supplied from the positional relation specifying section 210. The image storage section 250 may supply, to the judging section 220, the stored image together with the positional relation, upon request from the judging section 220.

Note that the judging section 220 may specify the displacement of the insertion section 20, based on the image contents of the image supplied from the image storage section 250, besides based on the displacement information supplied from the positional relation specifying section 210. For example, the judging section 220 may specify the displacement of the insertion section 20, from the plurality of images captured respectively at a plurality of different timings.

Figure 3:
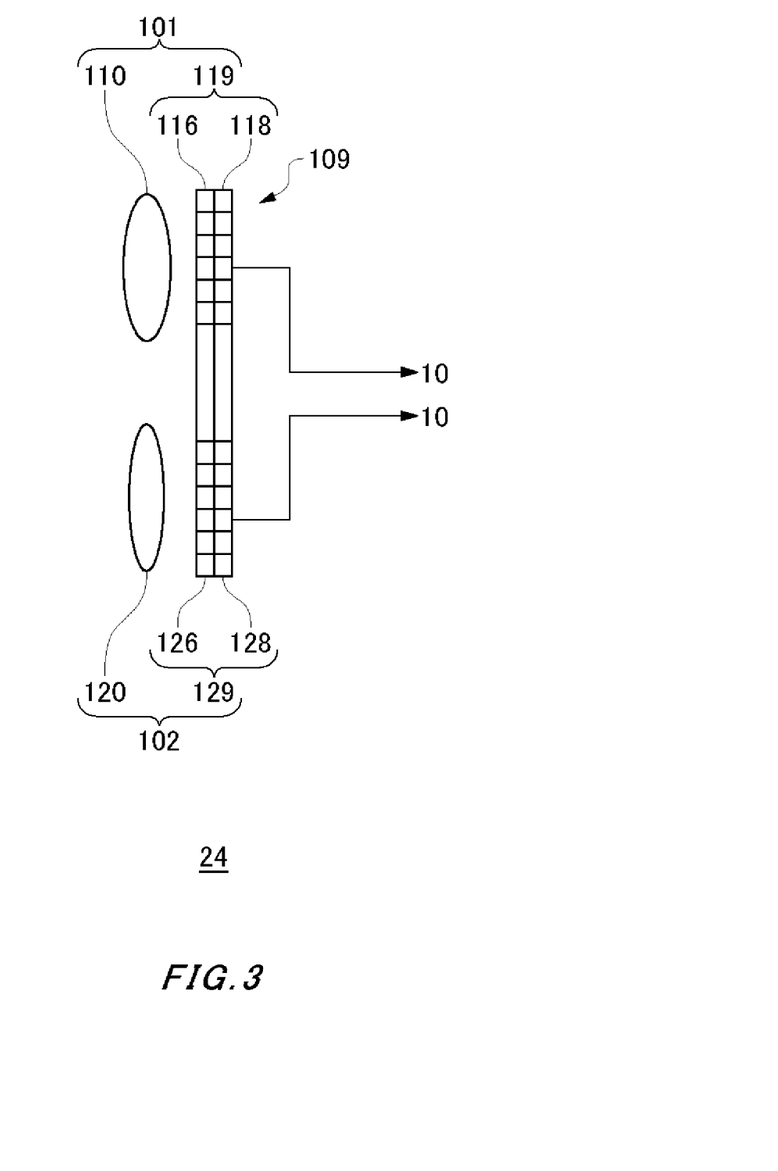
FIG. 3 schematically shows an exemplary block configuration of an image capturing section 24.

FIG. 3 schematically shows an exemplary block configuration of an image capturing section 24. The drawing shows the optical elements of the functional blocks of the image capturing section 24, which relate to the function of capturing images through the first lens 110 and the second lens 120. Specifically, the drawing shows a schematic sectional view taken at the plane including the optical axes of the first lens 110 and the second lens 120.

The image capturing section 24 includes a light receiving section 119, a second lens 120, and a second light receiving section 129, besides the first lens 110 and the second lens 120. The first lens 110 and the first light receiving section 119 function as a first image capturing system 101. The second lens 120 and the second light receiving section 129 function as a second image capturing system 102.

The first light receiving section 119 includes a first color filter array 116 and a first image capturing element array 118.

The second light receiving section 129 includes a second color filter array 126 and a second image capturing element array 128.

The first lens 110 has a first optical characteristic with respect to image capturing light. The second lens 120 has an optical axis at a different position from the optical axis of the first lens 110, and has a second optical characteristic with respect to image capturing light. Here, examples of the optical characteristics include optical response, an image forming characteristic, and a brightness characteristic. Examples of indices for the optical characteristics include focal depth, focal length, optical transfer function, F value, effective aperture, MTF, etc. Here, the second lens 120 is assumed to have a longer focal length than the first lens 110. For example, the second lens 120 is assumed to have a longer focal length than the first lens 110.

The following explains the optics configuration of the first image capturing system 101. The first lens 110 is an image forming lens, and forms an image of light from the living body 90, onto the first light receiving section 119. The first color filter array 116 includes a plurality of color filters that selectively transmit the light of a pre-set wavelength region. The first color filter array 116 is formed by arranging the plurality of color filters in a pre-set pattern. For example, the first color filter array 116 is formed by arranging the plurality of color filters in a matrix formation. The wavelength region transmitted through each color filter may be designed depending upon each purpose of image capturing of the first image capturing system 101. All the color filters may selectively transmit the light of specific wavelength regions, and may include a plurality types of color filters that respectively selectively transmit the light of wavelength regions different from each other.

The first image capturing element array 118 includes a plurality of image capturing elements receiving light from the living body 90 through the first lens 110. The plurality of image capturing elements included in the first image capturing element array 118 are provided to correspond to the plurality of color filters included in the first color filter array 116. From the subject light incident on the first color filter array 116, each image capturing element receives the light having been transmitted through the corresponding color filter. Each image capturing element outputs an image capturing signal having an intensity corresponding to the amount of received light.

The following explains the optics configuration of the second image capturing system 102. The second lens 120 is an image forming lens, and forms an image of light from the living body 90, onto the second light receiving section 129. The second color filter array 126 includes a plurality of color filters that selectively transmit the light of a pre-set wavelength region. The second color filter array 126 is formed by arranging the plurality of color filters in a pre-set pattern. For example, the second color filter array 126 is formed by arranging the plurality of color filters in a matrix formation. The wavelength region transmitted through each color filter may be designed depending upon each purpose of image capturing of the second image capturing system 102. All the color filters may selectively transmit the light of specific wavelength regions, and may include a plurality types of color filters that selectively transmit the light of wavelength regions different from each other.

The second image capturing element array 128 includes a plurality of image capturing elements receiving light from the living body 90 through the second lens 120. The plurality of image capturing elements included in the second image capturing element array 128 are provided to correspond to the plurality of color filters included in the second color filter array 126. From the subject light incident on the second color filter array 126, each image capturing element receives the light having been transmitted through the corresponding color filter. Each image capturing element outputs an image capturing signal having an intensity corresponding to the amount of received light.

The following explains the configurations of the first light receiving section 119 and the second light receiving section 129. The plurality of image capturing elements respectively included in the first light receiving section 119 and the second light receiving section 129 are provided on the same plane. For example, the plurality of image capturing elements included in the first image capturing element array 118 and the plurality of image capturing elements included in the second image capturing element array 128 are formed on the same substrate. For example, the plurality of image capturing elements included in the first image capturing element array 118 and the plurality of image capturing elements included in the second image capturing element array 128 are formed on a surface of the same substrate in the same process. The plurality of color filters included in the first color filter array 116 and the plurality of color filters included in the second color filter array 126 are also formed simultaneously in the same process on top of the corresponding image capturing elements. Accordingly, a single light receiving section 109 integrating the first light receiving section 119 and the second light receiving section 129 is manufactured. Each of the image capturing surface of the first light receiving section 119 and the image capturing surface of the second light receiving section 129 functions as a partial region of the image capturing surface of the light receiving section. Note that the first light receiving section 119 having the first image capturing element array 118 and the first color filter array 116 as well as the second light receiving section 129 having the second image capturing element array 128 and the second color filter array 126 can be separately manufactured from each other, and then assembled together. In this way, the plurality of image capturing elements included in the plurality of image capturing systems of the image capturing section 24 may be formed on the same substrate.

A plurality of image capturing elements respectively included in the first image capturing system 101 and the second image capturing system 102 are substantially simultaneously exposed to light. After exposure of each image capturing element to light, the output of the plurality of image capturing elements is read as an image capturing signal, and outputted to the control section 10. The reading circuit of an image capturing element may be formed on the same substrate as the image capturing element. One reading circuit may be provided for each of the image capturing systems, and the reading circuit may sequentially read image capturing signals from the plurality of image capturing elements included in each of the image capturing systems. Note that each image capturing system may be provided with their own reading circuit.

The plurality of image capturing elements included in each image capturing system may be a MOS image capturing element. When each image capturing element is a MOS image capturing element formed on a surface of the same substrate in the same process, the reading circuit can perform partial reading for each optical system included in each image capturing system. The plurality of image capturing elements included in each image capturing system may also be implemented by a solid-state image capturing element such as a CCD image capturing element, not limited to the MOS image capturing element.

As explained above, the second image capturing system 102 has an image capturing optical axis at a different position from that of the first image capturing system 101, and has a different image capturing characteristic from that of the first image capturing system 101. Although the explanation is omitted with respect to the present drawing, the image capturing section 24 has an optical element corresponding to the optical element shown in the drawing, as the functional block capturing an image through the third lens 130. Here, the functional block capturing an image through the third lens 130 is referred to as "third image capturing system." The third image capturing system has an image capturing optical axis different from those of the first image capturing system 101 and the second image capturing system 102, and has an image capturing characteristic different from those of the first image capturing system 101 and the second image capturing system 102.

The difference in image capturing characteristic between each image capturing system is due to at least one of the difference in optical characteristic of the optical system and the light receiving characteristic of the light receiving section 109. Here, the second lens 120 has a focal length longer than the first lens 110. The first image capturing system 101 and the second image capturing system 102 are assumed to capture an image using light of the same wavelength region. Specifically, the first image capturing system 101 and the second image capturing system 102 capture an image using light in a visible light wavelength region.

In addition, the third image capturing system has image capturing light in a wavelength region different from the image capturing light of the first image capturing system 101 and the second image capturing system 102. Specifically, the third image capturing system captures an image using infrared light in an infrared wavelength region. The color filter array included in the third image capturing system has a transmittance characteristic selectively transmitting infrared light. The third lens 130 has an image forming characteristic of forming an image of infrared light at a position of the light receiving section. In this way, the difference in image capturing characteristic may be a difference in wavelength region of light used in image capturing.

In the present embodiment, each image capturing system is assumed to have the above-explained image capturing characteristic. Besides this, in the image capturing section 24, the optical system included in each image capturing system may be different from the optical systems included in the other of image capturing systems, in at least one of the focal length, the focus distance, field depth, and the F value. In addition, the plurality of image capturing systems included in the image capturing section 24 may capture an image of the living body 90 by light in different wavelength regions from each other. In addition, the optical elements included in the first image capturing system 101, the second image capturing system 102, and the third image capturing system may be provided as a single image capturing module.

Figure 4:
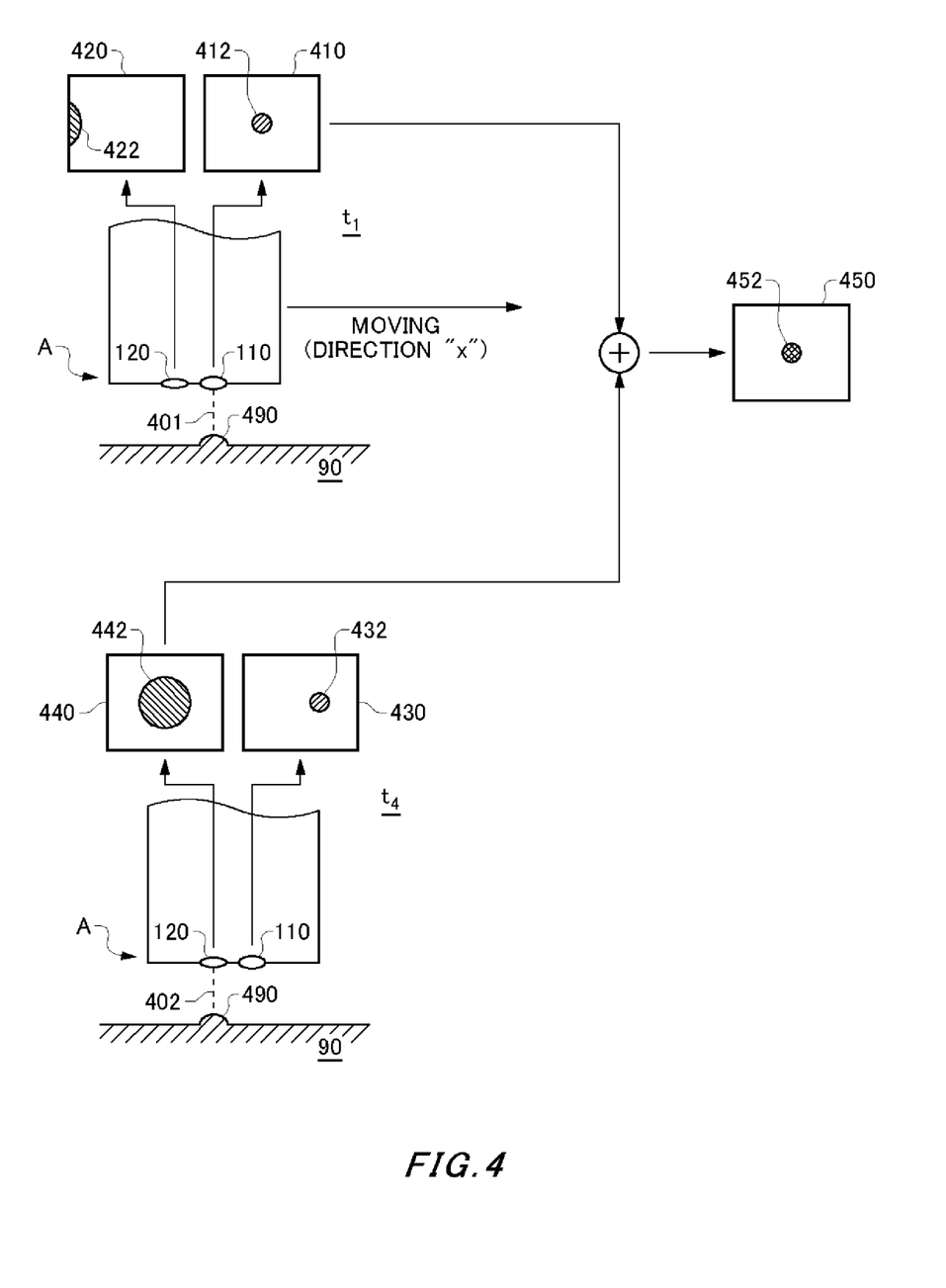
FIG. 4 schematically shows an example of image processing and image capturing control.

FIG. 4 schematically shows an example of image processing and image capturing control performed by the control section 10. In this drawing, Section A showing the tip of the insertion section 20 and the living body 90 are shown.

The image capturing control section 240 controls the image capturing section 24 to serially capture images of the living body 90. Here, the image capturing section 24 is assumed to have captured the image of the living body 90 at the time t1 (first timing). At the time t1, the optical axis 401 of the first lens 110 is assumed to be oriented towards a specific object 490 of the living body 90. The image capturing section 24 exposes the light receiving section 109 to light, thereby generating a first timing image 410 captured through the first lens 110 and a first timing image 420 captured through the second lens 120, as a first timing image. The first timing image 410 is temporarily stored in the image storage section 250.

When the user has inputted, to the operation information obtaining section 14, an instruction to move the tip of the insertion section 20 in the direction "x," the control section 10 moves the insertion section 20 in the direction "x" based on the displacement instruction from the operation information obtaining section 14. The positional relation specifying section 210 specifies the positional relation between the first lens 110 and the living body 90, based on the moving speed in the direction "x" and the time t1. Then, the positional relation specifying section 210 specifies the x coordinate of a pre-set coordinates system as the positional relation in relation to the living body 90. The coordinates system can be arbitrarily selected by the positional relation specifying section 210.

The judging section 220 can specify the amount of movement of the tip A in the direction "x" based on the time period that has elapsed from the time t1 and the displacement information in the direction "x." Based on this amount of movement, the judging section 220 predicts the timing at which the tip A will have moved by the distance between the first lens 110 and the second lens 120 in the direction "x." The judging section 220 outputs the image capturing instruction to the image capturing control section 240, so as to cause the image capturing section 24 to capture an image at the predicted timing. The image capturing section 24 exposes the light receiving section 109 to light at the time t4 corresponding to the second timing, by means of the image capturing control performed by the image capturing control section 240.

The optical axis 402 of the second lens 120 at the second timing is oriented towards the object 490. In other words, the relative position between the second lens 120 and the object 490 at the second timing is substantially equal to the relative position between the first lens 110 and the object 490 at the first timing. Therefore, the image of the object 490 can be captured at the timing at which the relative positions with respect to the object 490 substantially match between the first lens 110 and the second lens 120 using the first image capturing system 101 and the second image capturing system 102 that has higher resolution.

The image combining section 230 generates a combined image 450 by combing the first timing image 410 and the second timing image 440. The image combining section 230 performing the combining after correcting at least one of the first timing image 410 and the second timing image 440 based on the optical characteristic of the first lens 110 and the optical characteristic of the second lens 120. Specifically, the difference in focal length between the first lens 110 and the second lens 120 is corrected, thereby overlapping the corresponding image regions in the corrected images. The combined image 450 includes an image signal of the object image 442 captured through the second lens 120 having high resolution. Therefore, the combined object image 452 has higher resolution than the object image 412.

In this way, the positional relation specifying section 210 specifies a first positional relation between the first image capturing system 101 and the living body 90 at the first timing at which the first image capturing system 101 has captured the image of the subject. The judging section 220 judges whether a second positional relation between the second image capturing system 102 and the living body 90 matches more the first positional relation at the second timing than the first timing, based on the displacement of the insertion section 20 with respect to the living body 90 whose image has been captured by the first image capturing system 101, the positions of the image capturing axes of the first image capturing system 101 and the second image capturing system 102, and the first positional relation. Specifically, the judging section 220 judges whether the second positional relation matches more the first positional relation at the second timing than the first timing, based on the amount of movement indicated by the moving information supplied from the operation information obtaining section 14, the positions of the image capturing optical axes of the first image capturing system 101 and the second image capturing system 102, and the positional relation specified by the positional relation specifying section 210. When the judging section 220 has judged that the second positional relation matches more the first positional relation at the second timing than the first timing after the image capturing by the first image capturing system 101, the image capturing control section 240 controls the second image capturing system 102 to capture an image at the second timing. Then, the image combining section 230 combines the image of the living body 90 taken by the first image capturing system 101 at the first timing, with the image of the living body 90 taken by the second image capturing system 102 at the second timing.

Examples of the positional relation include, besides the x coordinate as stated above, the position in a plane facing the subject, the orientation of the optical axis of each image capturing system, and a distance up to the living body 90. Any positional relation may be adopted as long as it can specify the relative relation between each image capturing system and the living body 90.

Figure 5:
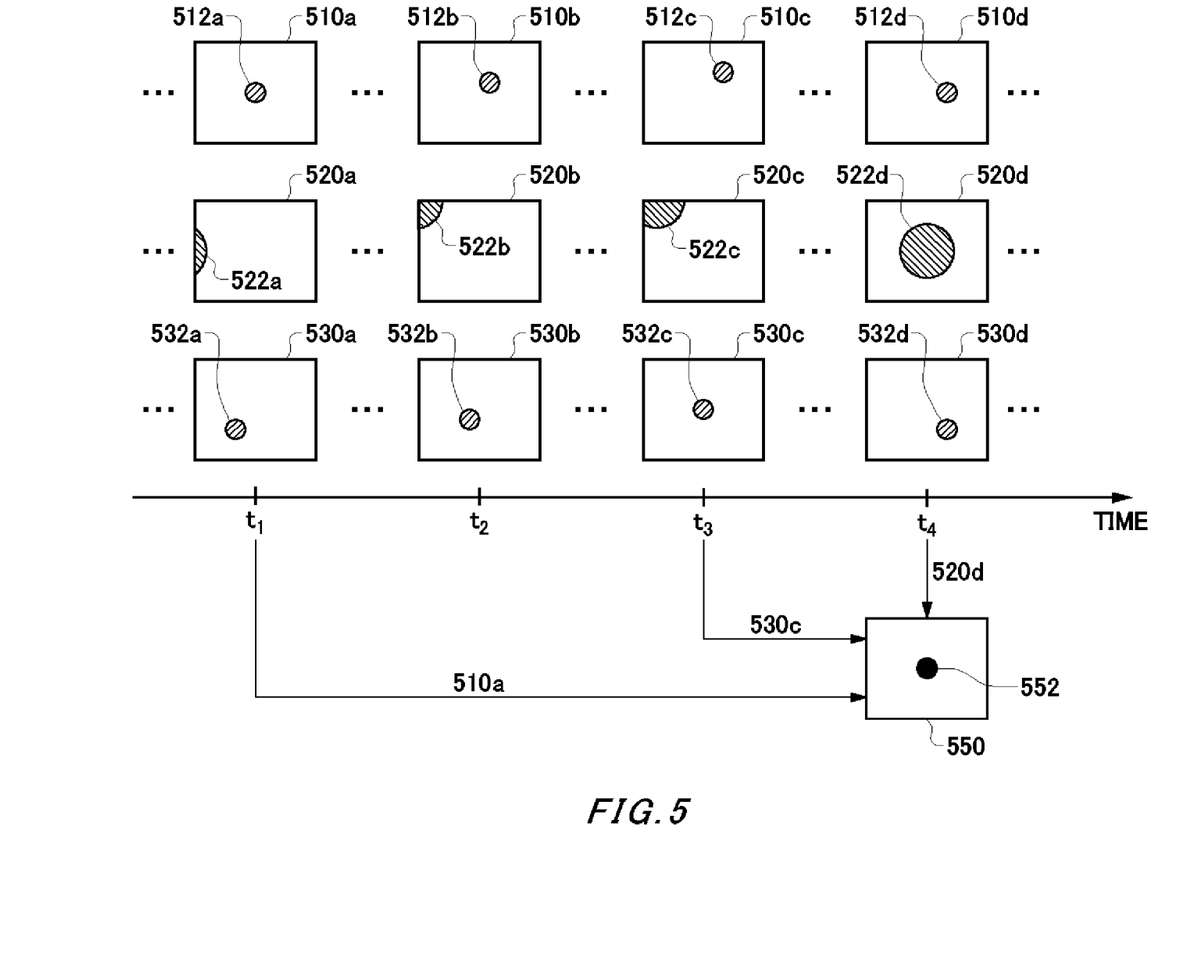
FIG. 5 schematically shows an example of image capturing control and image combining.

FIG. 5 schematically shows an example of image capturing control and image combining performed to the image capturing section 24. At the time t1, the first image capturing system 101, the second image capturing system 102, and the third image capturing system are respectively assumed to have captured the first-image-capturing-system image 510a, the second-image-capturing-system image 520a, and the third-image-capturing-system image 530a. The first-image-capturing-system image 510a and the second-image-capturing-system image 520a correspond to the first timing image 410 and the first timing image 420 in FIG. 4, respectively. The present drawing also relates to an example in which the second image capturing system 102 and the third image capturing system 103 are used to capture an image in a positional relation substantially matching the first positional relation between the first lens 110 and the object 490 when the first-image-capturing-system image 510a has been captured.

The judging section 220 serially judges the movement of the tip A of the insertion section 20. Then, when the positional relation of either the second image capturing system 102 or the third image capturing system has substantially matched the first positional relation, the judging section 220 outputs an image capturing instruction to the image capturing control section 240. The image capturing control section 240 supplies an image capturing instruction to the image capturing section 24 when a pre-set length of time period has elapsed (time t2) until receiving the image capturing instruction from the judging section 220. In the present drawing, the first-image-capturing-system image 510b, the second-image-capturing-system image 520b, and the third-image-capturing-system image 530b are examples of the image at the time t2. The first-image-capturing-system image 510b, the second-image-capturing-system image 520b, and the third-image-capturing-system image 530b can be outputted as a frame of a moving image.

Thereafter, at the time t3, the judging section 220 judges that the positional relation between the third image capturing system and the object 490 has substantially matched the positional relation between the first image capturing system 101 and the object 490 at the time t1. As a result of the judging section 220 outputting the image capturing instruction to the image capturing control section 240 at the time t3, the image capturing section 24 captures the first-image-capturing-system image 510c, the second-image-capturing-system image 520c, and the third-image-capturing-system image 530c. Thereafter, at the time t4, the judging section 220 judges that the positional relation between the second image capturing system 102 and the object 490 has substantially matched the positional relation between the first image capturing system 101 and the object 490 at the time t1. As a result of the judging section 220 outputting the image capturing instruction to the image capturing control section 240 at the time t4, the image capturing section captures the first-image-capturing-system image 510d, the second-image-capturing-system image 520d, and the third-image-capturing-system image 530d. The first-image-capturing-system image 510d and the second-image-capturing-system image 520d correspond to the second timing image 430 and the second timing image 440, respectively.

The image combining section 230 generates a combined image 550 by combining the first-image-capturing-system image 510a, the third-image-capturing-system image 530c, and the second-image-capturing-system image 520d. The combined object image 552 can be obtained by overlapping the object image 512a, the object image 532c, and the object image 522d. The combined object image 552 includes image information obtained as a result of the third image capturing system capturing an image by means of infrared light.

In this way, the judging section 220 judges whether the third positional relation between the third image capturing system and the living body 90 matches more the first positional relation at the third timing than the first timing, based on the displacement of the insertion section 20, the positions of the image capturing optical axes of first image capturing system 101 and the third image capturing system, and the first positional relation. Then, the image combining section 230 combines the image of the living body 90 captured by the first image capturing system 101 at the first timing, the second image of the subject captured by the second image capturing system 102 at the second timing, and the third image of the living body 90 captured by the third image capturing system at the third timing.

Figure 6:
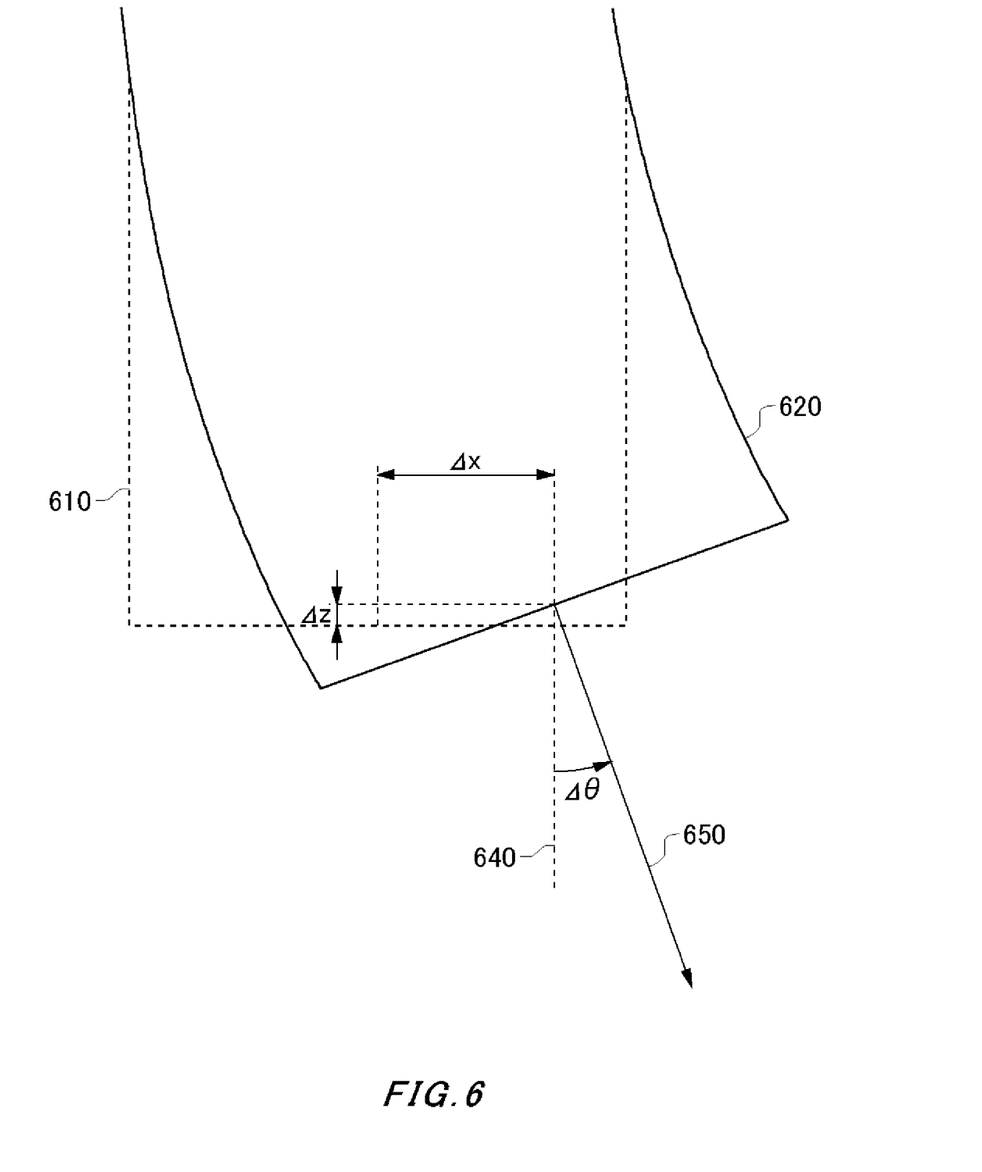
FIG. 6 shows an exemplary index of the positional relation.

FIG. 6 shows an exemplary index of the positional relation. Here, cases where the tip of the insertion section 20 is in the state 610 and in the state 620 are illustrated. The position of the center of the end surface of the insertion section 20 is displaced, due to the change the state of the tip according to the control amount of the insertion section 20 (e.g., the amount of insertion or the amount of bending of the insertion section 20 described above).

An example of the index of the central position of the end surface is the amount of displacement between the central position of the end surface in the state 610 and the central position of the end surface in the state 620. In the present drawing, the amount of displacement in the direction "x" is represented by $\Delta x$, and the amount of displacement in the direction "z" is represented by $\Delta z$. The amount of displacement in the direction "y" vertical to the direction "x" and the direction "z" can be also used as an index of the position. An example of the index of the image capturing direction is the change amount $\Delta \theta$ of the angle formed between the image capturing direction 640 in the state 610 and the image capturing direction 650 in the state 620. The change amount $\Delta\theta$ can be defined for both of the direction "x" and the direction "z."

When the living body 90 is still, these indices can be directly used as indices representing the relative positional relation with respect to the living body 90. The positional relation between each lens and the living body 90 can be quantified based on these indices and the relative position of the optical axes of the lenses. While the living body 90 itself is being displaced, the amount of displacement of the living body 90 may be occasionally specified from the images serially captured by the image capturing section 24. Therefore, the positional relation specifying section 210 can specify the positional relation between each lens and the living body 90, based on at least one of the control amount of the tip of the insertion section 20 and the images serially captured by the image capturing section 24. Likewise, the judging section 220 can specify the positional relation between each lens and the living body 90, based on at least one of the control amount of the tip of the insertion section 20 and the images serially captured by the image capturing section 24, thereby judging whether the positional relations match.

The amount of displacement in the direction "x," the amount of displacement in the direction "y," and the amount of displacement in the direction "z" correspond to the relative position between each image capturing system and the living body 90. In addition, the change amount $\Delta\theta$ of the angle corresponds to the orientation of the image capturing axis of each image capturing system. Therefore, the positional relation specifying section 210 can specify, as the first positional relation, the relative position of the first image capturing system 101 with respect to the living body 90 and the orientation of the image capturing optical axis of the first image capturing system 101 at the first timing. Then, the judging section 220 can judge whether the relative position of the second image capturing system 102 with respect to the living body 90 and the orientation of the image capturing optical axis of the second image capturing system 102 matches more the first positional relation at the second timing than the first timing.

Note that when the living body 90 is still, the amount of displacement in the direction "z" corresponds to the distance up to the living body 90. Therefore, if displaced in the direction "z," the central position of the image capturing range does not substantially change, although the width of the image capturing range changes. As opposed to this, the amount of displacement in the direction "x," the amount of displacement in the direction "y," and the change amount of the angle substantially changes the central position of the image capturing range. Therefore, the judging section 220 may perform the positional relation judgment, by giving more weight to the amount of displacement in the direction "x," the amount of displacement in the direction "y," and the displacement amount of the angle, than the weight to the amount of displacement in the direction "z."

In the above-stated description, the judging section 220 has been explained to output an image capturing instruction at the timing in which the first positional relation matches the second positional relation. Not limited to this example, the judging section 220 may also select, from among the images stored in the image storage section 250, the image having been already captured at the second positional relation matching the first positional relation. In such a case, the image combining section 230 can combine the selected image with the image newly captured in the first positional relation.

In other words, the image storage section 250 stores a plurality of images captured by the second image capturing system 102 at different timings from each other. For example, the first image capturing system 101 and the second image capturing system 102 serially capture images substantially at the same image capturing timing. Then, the image storage section 250 stores the plurality of images respectively captured by the first image capturing system 101 and the second image capturing system 102, in association with information indicating the image capturing timing of them. When the first image capturing system 101 has captured the image of the living body 90 in the first positional relation, the judging section 220 judges, for each image stored in the image storage section 250, whether the second positional relation at the timing at which each image has been captured matches the first positional relation more than the first timing. Then, the image combining section 230 selects, from among the images that are judged to match the first positional relation, the image whose matching degree of the second positional relation with respect to the first positional relation is greater than a pre-set value, and combines the selected image with the first image. By controlling in the above manner, the images captured in the corresponding positional relation can be selected, even without performing dynamic control of the image capturing timings.

In the above description, the image capturing section 24 was explained to include three image capturing systems. Not limited to such a configuration, the image capturing section 24 may include two or four image capturing systems. In addition, in the present embodiment, an endoscope system was taken as an example of the image capturing apparatus according to the present invention. However, not limited to the endoscope system, various image capturing appliances such as a portable telephone including a camera function, a digital still camera, and a digital video camera can be included as the image capturing apparatus according to the present invention.

While the embodiment(s) of the present invention has (have) been described, the technical scope of the invention is not limited to the above described embodiment(s). It is apparent to persons skilled in the art that various alterations and improvements can be added to the above-described embodiment(s). It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

What is claimed is:

1. An image capturing apparatus comprising:
   an image capturing section that includes a first image capturing system including a first lens having a first image capturing optical axis and a second image capturing system, the second image capturing system including a second lens having a second image capturing optical axis on a different position from the first image capturing optical axis of the first image capturing system and having a different resolution from that of the first image capturing system;
   a positional relation specifying section that specifies a first positional relation between the first lens and a subject at a first timing at which the first image capturing system has captured an image of the subject;

a judging section that judges whether a second positional relation between the second lens and the subject matches more the first positional relation at a second timing than the first timing, based on a displacement of the image capturing apparatus with respect to the subject captured by the first image capturing system, positions of the first and second image capturing optical axes respectively of the first image capturing system and the second image capturing system, and the first positional relation;

an image capturing control section that controls the second image capturing system to perform image capturing at the second timing, when the judging section has judged that the second positional relation matches more the first positional relation at the second timing than the first timing after the first image capturing system has performed image capturing at the first timing; and an image combining section that combines a first image of the subject captured by the first image capturing system at the first timing, with a second image of the subject captured by the second image capturing system at the second timing.

2. The image capturing apparatus according to claim 1, further comprising:

a movement information obtaining section that obtains movement information indicating an amount of movement of the image capturing apparatus, wherein the judging section judges whether the second positional relation matches more the first positional relation at the second timing than the first timing, based on the amount of movement indicated by the movement information, the positions of the image capturing optical axes respectively of the first image capturing system and the second image capturing system, and a positional relation specified by the positional relation specifying section.

3. The image capturing apparatus according to claim 1, wherein the positional relation specifying section specifies, as the first positional relation, a relative position of the first image capturing system with respect to the subject and an orientation of the image capturing optical axis of the first image capturing system at the first timing, and the judging section judges whether the relative position of the second image capturing system with respect to the subject and the orientation of the image capturing optical axis of the second image capturing system match more the first positional relation at the second timing than the first timing.

4. The image capturing apparatus according to claim 1, further comprising:

an image storage section that stores a plurality of images captured by the second image capturing system at different timings, wherein for each image stored in the image storage section, the judging section judges whether the second positional relation in a timing at which the image has been captured matches the first positional relation more than the first timing, and the image combining section selects, from among the images whose second positional relation is judged to match more the first positional relation, an image whose matching degree of the second positional relation with respect to the first positional relation is greater than a pre-set value, and combines the selected image with the first image.

5. The image capturing apparatus according to claim 4, wherein the first image capturing system and the second image capturing system capture serially capture images at substantially the same image capturing timings as each other, and the image storage section stores the plurality of images respectively captured by the first image capturing system and the second image capturing system, in association with information indicating respective image capturing timings.

6. The image capturing apparatus according to claim 1, wherein the image capturing section further includes a third image capturing system whose image capturing optical axis and image capturing characteristic are different from image capturing optical axes and image capturing characteristics respectively of the first image capturing system and the second image capturing system, wherein the judging section further judges whether a third positional relation between the third image capturing system and the subject matches more the first positional relation at a third timing than the first timing, based on the displacement, the positions of image capturing optical axes respectively of the first image capturing system and the third image capturing system, and the first positional relation, and the image combining section combines the first image and the second image with a third image of the subject captured by the third image capturing system at the third timing.

7. The image capturing apparatus according to claim 1, wherein a plurality of image capturing systems included in the image capturing section capture an image of the subject by means of rays of light in wavelength regions different from each other.

8. The image capturing apparatus according to claim 1, wherein in the image capturing section, an optical system included in each image capturing system is different at least in one of focal length, focus distance, field depth, and F value, from the optical systems included in the other image capturing systems.

9. The image capturing apparatus according to claim 1, wherein a plurality of image capturing systems included in the image capturing section respectively include a plurality of image capturing elements receiving light from the subject, and the plurality of image capturing elements respectively included in the plurality of image capturing systems included in the image capturing section are formed on the same substrate.

10. An endoscope system for capturing an image of a living body as the subject, comprising:

the image capturing apparatus according to claim 1.

11. The image capturing apparatus according to claim 8, wherein a plurality of image capturing systems included in the image capturing section capture an image of the subject by means of rays of light in wavelength regions different from each other.

12. The image capturing apparatus according to claim 11, wherein the plurality of image capturing systems includes a first image capturing system that captures an image by means of rays of light in a red wavelength region, a second image capturing system that captures an image by means of rays of light in a green wavelength region, and a third image capturing system that captures an image by means of rays of light in a blue wavelength region.

13. An apparatus comprising:
- a first image capturing system including a first lens having a first optical axis and a first image capturing resolution;
- a second image capturing system in a fixed position relative to the first image capturing system, the second image capturing system having a second lens and second image capturing optical axis, which is different than the first image capturing optical axis, and a second image capturing resolution, which is different than the first image capturing resolution;
- a positional relation specifying section that specifies a first positional relation between the first image capturing lens and a subject at a first timing at which the first image capturing system has captured an image of the subject;
- a judging section that judges whether a second positional relation between the second image capturing lens and the subject at a second timing is substantially equal to the first positional relation, based on a displacement of at least one of the first image capturing system and the second image capturing system from the first timing to the second timing, a relative position of the second image capturing optical axis with respect to the first image capturing optical axis, and the first positional relation; and
- an image combining section that combines a first image of the subject captured by the first image capturing system at the first timing, with a second image of the subject captured by the second image capturing system at the second timing.

14. The apparatus according to claim 13, further comprising:
- a movement information obtaining section that obtains an amount of movement of the second image capturing system,
- wherein the judging section judges whether the second positional relation is substantially equal to the first positional relation, based on the amount of movement of the second image capturing system from the first timing to the second timing, the relative position of the second image capturing optical axis with respect to the first image capturing optical axis, and the first positional relation.

15. The apparatus according to claim 13, wherein the positional relation specifying section further specifies an orientation of the image capturing optical axis of the first image capturing system at the first timing, and the judging section judges based further on an orientation of the image capturing optical axis of the second image capturing system at the second timing.

16. The apparatus according to claim 13, further comprising:
- an image capturing control section that controls the second image capturing system to perform image capturing when the judging section has judged that the second positional relation is substantially equal to the first positional relation.

17. The apparatus according to claim 13, wherein the first and second image capturing systems are different in at least one of focal length, focus distance, field depth, and F value.

18. The apparatus according to claim 17, wherein the first image capturing system captures a wavelength region of light that is different from the second image capturing system.

19. The apparatus according to claim 18, wherein the wavelength region is a red wavelength region, a green wavelength region, or a blue wavelength region.

* * * * *